United States Patent [19]

Liu et al.

[11] 4,197,405

[45] Apr. 8, 1980

[54] THERMOLYSIS OF 3'-(ARYL)-SPIRO[ISOBENZOFURAN-1(3H),5'(4'H)-ISOXAZOL]-3-ONE

[75] Inventors: Kou-Chang Liu, Creve Coeur; Robert K. Howe, Bridgeton, both of Mo.

[73] Assignee: Monsanto Company, St. Louis, Mo.

[21] Appl. No.: 13,853

[22] Filed: Feb. 22, 1979

[51] Int. Cl.² .................................. C07D 263/32
[52] U.S. Cl. .................................. 548/247
[58] Field of Search .................................. 260/307 H

[56] References Cited

U.S. PATENT DOCUMENTS

| | | | |
|---|---|---|---|
| 3,947,263 | 3/1976 | Brouwer et al. | 71/76 |
| 3,964,896 | 6/1976 | Brouwer et al. | 71/92 |
| 4,032,644 | 6/1977 | Nadelson | 424/272 |
| 4,135,910 | 1/1979 | Howe | 71/92 |
| 4,140,515 | 2/1979 | Howe | 71/88 |

FOREIGN PATENT DOCUMENTS 1494877  12/1977  United Kingdom .............. 260/307 H

*Primary Examiner*—Anton H. Sutto
*Attorney, Agent, or Firm*—Richard H. Shear; Donald W. Peterson

[57] ABSTRACT

2-(3-Aryl-5-isoxazolyl)benzoic acids are prepared by thermolysis of 3'-(Aryl)-spiro[isobenzofuran-1(3H),5'(4'H)-isoxazol]-3-one.

7 Claims, No Drawings

THERMOLYSIS OF 3'-(ARYL)-SPIRO[ISOBENZOFURAN-1(3H),5'(4'H)-ISOXAZOL]-3-ONE

This invention relates to the preparation of 2-(3-Aryl-5-isoxazolyl) benzoic acid by thermolysis of 3'-(Aryl)-spiro[isobenzofuran-1(3H),5'(4'H)-isoxazol]-3-one. More specifically, the benzoic acids may be prepared in accordance with the following reaction scheme:

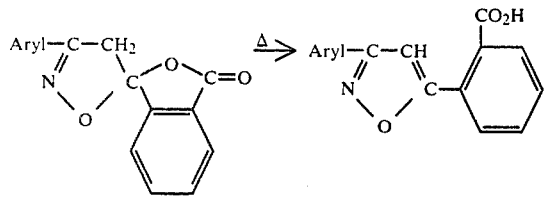

The 3-(Aryl)-spiro[isobenzofuran-1(3H),5'(4'H)-isoxazol]-3-one precursor has been disclosed in our copending application, Ser. No. 971,462, filed Dec. 20, 1978, and is prepared as disclosed therein by reaction of a nitrile oxide with 3-methylenephthalide in accordance with the following equation:

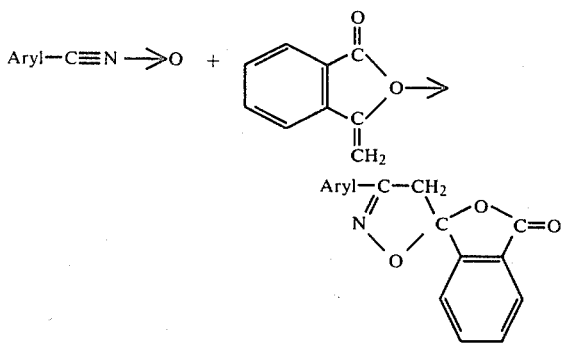

The benzoic acids are themselves useful as plant growth regulants or may be converted by esterification to esters which are useful as plant growth regulants as taught by U.S. patent application Ser. No. 796,248, filed May 12, 1977, now abandoned, U.S. patent application Ser. No. 907,069, filed May 18, 1978 and U.S. patent application Ser. No. 966,403, filed Dec. 4, 1978 which are incorporated by reference.

To prepare the benzoic acid, the spiro compound should be heated at atmospheric pressure above its melting point for a short period of time, normally less than one hour.

Since the Aryl radical takes no appreciable part in the thermolysis, any aromatic compound including heteroaryl may be used. Preferably, however, Aryl is a radical of the following formula

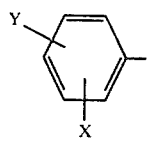

wherein X and Y are independently selected from the group consisting of hydrogen, halogen, lower alkyl, lower alkoxy, halo-lower-alkyl, phenoxy and phenyl.

As used herein, the terms "lower alkyl" and "lower alkoxy" are understood to include those alkyl and alkoxy groups having up to five carbon atoms, inclusive. Both straight as well as branched chain alkyl groups are contemplated. The term "halo-lower-alkyl" as used herein is understood to mean those lower alkyl groups in which at least one and perhaps all of the hydrogen atoms have been replaced by halogen atoms. It is to be clearly understood that trifluoromethyl is contemplated as being a halo-lower-alkyl moiety.

The term "halogen" as used herein includes chlorine, bromine, fluorine and iodine.

In order to illustrate the novel aspects of the present invention, the following examples are presented and are not intended as a limitation with respect to the scope thereof.

EXAMPLE 1

3'-(m-Trifluoromethylphenyl)-spiro[isobenzofuran-1(3H),5'(4'H)-isoxazol]-3-one (2 grams) was placed in a test tube and heated in an oil bath at 200°–220° C. for two hours. NMR indicated that the reaction was complete and that the product was the desired acid. The crude product was a yellow solid, m.p. 173°–175° C. Recrystallization from acetonitrile afforded 1.25 grams of a yellow solid; m.p. 177°–178° C.

EXAMPLE 2

3'-(p-Trifluoromethylphenyl)-spiro[isobenzofuran-1(3H),5'(4'H)-isoxazol]-3-one (1.35 grams) was placed in a test tube and heated in an oil bath at 200°–220° C. for 35 minutes. NMR indicated that the reaction was complete and that the desired acid was prepared as a light brown solid; m.p. 198°–202° C. Recrystallization from acetonitrile afforded 0.92 grams of a white-yellow solid; m.p. 205°–207° C.

Anal. Calc'd. for $C_{17}H_{10}F_3NO_3$: C, 61.27; H, 3.02. Found: C, 61.22; H, 3.07.

EXAMPLE 3

3'-(2,4-Dichlorophenyl)-spiro[isobenzofuran-1(3H),5'(4'H)-isoxazol]-3-one (1.35 grams) was placed in a test tube and heated with an oil bath at a temperature of 185°–190° C. for about 15 minutes. NMR indicated the reaction was complete and that the desired acid was obtained as a white solid; m.p. 181°–183° C. Recrystallization from acetonitrile resulted in 0.75 grams of a white solid; m.p. 182°–183° C.

Anal. Calc'd. for $C_{16}H_9NCl_2O_3$: C, 57.86; H, 2.73. Found: C, 57.61; H, 2.79.

The above examples illustrate that heating the spiro compounds for short periods of time at a temperature just above their melting point results in the conversion of said compound to the desired acid. In industrial applications, it may be found to be convenient to dissolve the spiro compound in a suitable solvent and heat the solution to convert the spiro compound to the desired acid. The amount of heat applied is not critical but should be that amount which is sufficient to convert said spiro compound to the desired acid. Heating the solution from temperatures just above room temperature, e.g. 30° C., to the reflux temperature of the solution may be feasible but conversion at temperatures below about 100° C. will be very slow. Temperatures above 100° C., and especially 125° C. up to said reflux temperature, will result in rather rapid conversion. The solvent utilized is not critical. Any solvent which is inert to the spiro compound and the desired acid and has a sufficiently high boiling point (e.g., above 80° C.) will suffice. Examples of such suitable solvents are o-dichlorobenzene, dodecane, 1,2,3-trimethylbenzene, benzyl ethyl ether, 1,1,2-tribromoethane, 5-ethyl-4-propyl-1,3-dioxane and the like.

EXAMPLE 4

A solution of 3'-(m-trifluoromethylphenyl)-spiro-[isobenzofuran-1(3H),5'(4'H)-isoxazol]-3-one (1 gram) in 20 ml. of o-dichlorobenzene was held at reflux for 3.5 hours, cooled and concentrated under vacuum to give a yellow solid. NMR indicated that the reaction was not yet complete. The solid was redissolved in 20 ml. of o-dichlorobenzene and the solution was held at reflux for another 3 hours, cooled and concentrated under vacuum to give a quantitative yield of the desired acid as a pale yellow solid; m.p. 172°–174° C.

The present invention, therefore, provides a rather fast, efficient manner for providing 2-(3-Aryl-5-isoxazolyl)-benzoic acid which is useful as a plant growth regulant or can be esterified to provide other plant growth regulants.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A process for preparing 2-(3-Aryl-5-isoxazolyl)-benzoic acid having the formula

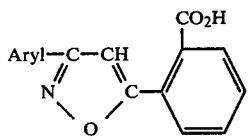

which comprises heating 3'-(Aryl)-spiro[isobenzofuran-1(3H),5'(4'H)-isoxazol]-3-one having the formula

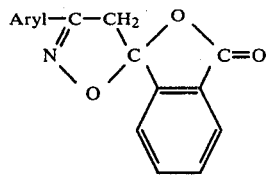

at a temperature sufficient to convert said spiro compound to said acid.

2. A process according to claim 1 wherein said spiro compound is dissolved in a suitable inert solvent and heated at a temperature ranging from 30° C. to the reflux temperature of the solution.

3. A process according to claim 2 wherein said temperature ranges from 100° C. to the reflux temperature of the solution.

4. A process according to claim 2 wherein said temperature ranges from 125° C. to the reflux temperature of the solution.

5. A process according to claim 2 wherein said temperature is the reflux temperature of the solution.

6. A process according to claim 1 wherein said Aryl is

wherein X and Y are independently selected from the group consisting of hydrogen, halogen, lower alkyl, lower alkoxy, halo-lower-alkyl, phenoxy and phenyl.

7. A process according to claim 6 wherein X is hydrogen and Y is trifluoromethyl.

* * * * *